United States Patent
Dehler

(10) Patent No.: US 8,225,495 B2
(45) Date of Patent: Jul. 24, 2012

(54) LOCALIZING UNIT FOR AN X-RAY DIAGNOSTIC SYSTEM WITH A STERILE DRAPE

(75) Inventor: Juergen Dehler, Forchheim (DE)

(73) Assignee: Ziehm Imaging GmbH, Nuremberg (DE)

( * ) Notice: Subject to any disclaimer, the term of this patent is extended or adjusted under 35 U.S.C. 154(b) by 1028 days.

(21) Appl. No.: 12/114,672

(22) Filed: May 2, 2008

(65) Prior Publication Data

US 2008/0285721 A1    Nov. 20, 2008

(30) Foreign Application Priority Data

May 5, 2007 (DE) .......................... 10 2007 021 182

(51) Int. Cl.
*B23P 21/00* (2006.01)
*H05G 1/02* (2006.01)
(52) U.S. Cl. .......................................... 29/722; 378/193
(58) Field of Classification Search ............... 29/525.01, 29/525.02, 525.11, 559, 714, 721, 722, 432; 178/193; 606/32–41; 600/121, 125; 378/193
See application file for complete search history.

(56) References Cited

U.S. PATENT DOCUMENTS

| 7,122,032 B2 | 10/2006 | Shinmura et al. |
| 2003/0216723 A1 | 11/2003 | Shinmura et al. |

FOREIGN PATENT DOCUMENTS

| DE | 41 08 593 | 9/1992 |
| DE | 196 40 993 | 4/1997 |
| DE | 199 08 903 | 9/2000 |
| DE | 199 17 867 | 11/2000 |
| DE | 101 39 329 | 3/2003 |
| DE | 102 15 808 | 11/2003 |
| DE | 103 60 025 | 7/2005 |
| EP | 1 190 679 | 3/2002 |

*Primary Examiner* — John C Hong
(74) *Attorney, Agent, or Firm* — Knobbe, Martens, Olson & Bear, LLP

(57) ABSTRACT

A localizing unit for an X-ray diagnostic system covered with a sterile drape is provided. In one embodiment, the localizing unit can be sterilized and has an adapter, which includes a mechanism for puncturing the sterile drape and a mechanism for temporarily securing the sterile drape on a housing of the X-ray diagnostic system. The adapter may be detachably held in predetermined holders on the housing of the X-ray diagnostic system and may be positioned on the housing in a reproducible manner. In some embodiments, the mechanism for temporarily securing the sterile drape on the housing includes an elastically deformable, surrounding seal, which upon positioning the adapter, produces a force on the sterile drape in a direction perpendicular to the surface of the housing.

8 Claims, 3 Drawing Sheets

LOCALIZING UNIT FOR AN X-RAY DIAGNOSTIC SYSTEM WITH A STERILE DRAPE

CROSS-REFERENCE TO RELATED APPLICATIONS

This application claims the right of priority under 35 U.S.C. §119(a)-(d) to German Patent Application No. DE 10 2007 021 182.3, filed May 5, 2007, the entire disclosure of which is hereby incorporated by reference herein and made part of this specification.

BACKGROUND

1. Field

The subject matter of the present application relates generally to a localizing unit for a diagnostic system at least partially covered with a sterile drape.

2. Description of the Related Art

Medical interventions involving living subjects are increasingly performed using navigation assistance provided by a navigation support system. In some navigation support systems, a surgical instrument is guided by means of a position detection system relative to a tissue region of the subject undergoing treatment. Navigation assistance is of particular interest in body regions that cannot be visually inspected by the surgeon, such as when the instrument is inserted into the interior of the subject. For this purpose, the instrument, for example, a catheter, is guided in a virtual 3D volume generated by means of an imaging method prior to or during surgery. For example, an X-ray diagnostic machine may be used to generate a series of 2D projection images having a known projection geometry, and the 2D images may be used to generate a 3D volume data set. The 3D volume data set is transmitted to the navigation system, which is equipped with a position detection system for detecting positions of the markers. For high-precision navigation, the coordinate system of the position detection system can be aligned and/or oriented with the coordinate system of the 3D volume data set in a process commonly known as "registration."

Various X-ray diagnostic devices are known in which a portion of the device is provided with marks that can be detected by a position detection system.

German Patent DE 196 40 993 A1 (Offenlegungsschrift) describes a medical therapy and/or diagnosis device enclosed by a sterilization sheath. A sterilizable and operationally detachable mounting element is coupled above the sterilization sheath. The mounting element has an operating position on the medical therapy and/or diagnosis device such that a defined positional relationship is produced between the device and the mounting element. When the mounting element is coupled to the sterilization sheath, fitting pins penetrate the sheath and are held in fitting pin recesses. The mounting element can be used to fasten the sterilization sheath to the therapy and/or diagnosis device by a knurled-head screw.

U.S. Pat. No. 7,122,032 B2, an operating microscope with a sterile sheath is described. A sterilizable electrical plug connector is used to puncture the sterile sheath. The electrical plug connector has a flange that affixes the sterile sheath on the microscope housing.

German Patent DE 102 15 808 B4 describes an X-ray device having a mark arrangement on the holder for a C-arm. The mark arrangement can be detected with a position detection system, and the spatial configuration and position of the X-ray device can be determined.

German Patents DE 103 60 025 B4 and DE 101 39 329 B4 describe X-ray diagnosis devices in which an X-ray receiver has a mark arrangement.

German Patent DE 199 08 903 C2 describes a localizing unit for imaging and describes positioning devices, which have, on a base plate, marks and sensors for position detection with different localizing systems.

German Patent DE 196 25 411 C2 describes a medical unit having a detachable and displaceable handle and a sterile drape.

It is known from actual practice using localizing units for diagnostic devices with sterile drapes that a position detection system may have difficulty in detecting a localizing unit through the drape. Accordingly, in actual practice, a substantially transparent sterile drape is positioned close to the localizing unit. The drape may be temporarily affixed in position, as described, for example, in the second aspect of the invention of DE 196 40 993 A1. Such positioning disadvantageously may cause the sterile drape to be punctured with subsequent loss of sterility, particularly with localizing units or marks having small radii of curvature.

In implementations in which the localizing unit is held in the operating position, and the drape is positioned on the housing of the diagnostic device, the mechanical characteristics of the sterile drape in its actual orientation on the device may be accounted for when the position and orientation of the localizing unit is determined in the coordinate system of the diagnostic device. Mechanical characteristics may include, for example, thickness, compressibility, arrangement of folds, welding or seam edges, and so forth. In actual practice, such positioning may be difficult, because, for example, freedom from folds of the sterile drape can be controlled only with great difficulty in an area in which the drape is attached to the system.

SUMMARY

Because of the foregoing (and other) challenges and limitations, there is a need for a localizing unit for an X-ray diagnostic system covered at least partially with a sterile drape such that the localizing unit is operable substantially independently of the characteristics of the sterile drape. The localizing unit may comprise an adapter configured to permit detachable and reproducible positioning of the adapter on the system.

In certain embodiments, a sterilizable localizing unit is adapted for detachable and reproducible positioning on a housing of a nonsterile surgical X-ray diagnosis system, which is covered at least in part with a sterile drape. The localizing unit may comprise an adapter having at least one mark that can be detected by a position detection system. In certain such embodiments, the adapter comprises means for puncturing the sterile drape, means for the detachable and reproducible positioning of the adapter on the housing, and means for temporarily securing the sterile drape on the housing while the adapter is positioned on the housing. The means for temporarily securing the sterile drape on the housing may comprise an elastically deformable, surrounding seal, which produces a force on the sterile drape in a direction perpendicular to the surface of the housing during the positioning of the adapter.

In some embodiments of the sterilizable localizing unit, the means for the detachable and reproducible positioning of the adapter comprises a pushbutton with which the adapter can be locked or unlocked with respect to the housing. In some embodiments, the pushbutton comprises a spring, a cone, and one or more ball bearings. The spring provides a resistance force against the pushbutton.

In some embodiments of the sterilizable localizing unit, the means for the detachable and reproducible positioning of the adapter comprises a threaded portion that can be screwed into the housing. The adapter may also comprise a stop shoulder adapted to stop on the housing.

In some embodiments of the sterilizable localizing unit, the adapter comprises a holding plate comprising one or more marks that are arranged in predetermined positions relative to a coordinate system of the adapter.

In some embodiments of the sterilizable localizing unit, the adapter comprises at least one mark capable of being scanned by a pointer of the position detection system.

In some embodiments of the sterilizable localizing unit, the adapter has at least one mark that comprises an auto-reflection target capable of being detected by the position detection system.

An embodiment of an adapter for removably attaching a sterile drape to a medical diagnostic system is provided. The adapter comprises a lower portion configured for removable attachment to a borehole in a housing of the medical diagnostic system. The lower portion comprises a tip configured to puncture the sterile drape, and the lower portion comprises a locking mechanism configured to releasably lock the adapter into a predetermined position on the medical diagnostic system. Preferably, the adapter also comprises an upper portion having one or more markers capable of being detected by a position detection system. Preferably, the adapter comprises a seal configured to secure a portion of the sterile drape between a portion of the adapter and the housing of the medical diagnostic system.

In some embodiments of the adapter, the locking mechanism comprises threads configured to engage complementary threads in the borehole of the housing. In some embodiments of the adapter, the locking mechanism further comprises a stop configured to limit engagement of the lower portion of the adapter and the borehole.

In some embodiments of the adapter, the locking mechanism comprises a pushbutton that can be actuated between a locked position and an unlocked position. The pushbutton may comprise a user-actuatable button, a conical member capable of moving along a longitudinal axis, a spring configured to provide a spring force along the longitudinal axis, and one or more ball bearings capable of moving radially toward and away from the longitudinal axis in response to movement of the conical member. In some embodiments, when the pushbutton is in the locked position, an outer surface of the conical member provides a radial-directed force on the one or more ball bearings. In some embodiments, when the pushbutton is in the unlocked position, the button is depressed thereby moving the conical member in the longitudinal direction and thereby reducing the radial-directed force on the one or more ball bearings.

In some embodiments of the adapter, the seal comprises an elastically deformable material.

An embodiment of a method for temporarily securing a sterile drape to a nonsterile surgical X-ray diagnosis system is provided. The method comprises providing a sterilizable localizing unit having an adapter. Preferably, the adapter has at least one mark that can be detected by a position detection system. Preferably, the adapter comprises means for puncturing the sterile drape, means for the detachable and reproducible positioning of the adapter on a housing, and means for temporarily securing the sterile drape on the housing while the adapter is positioned on the housing. The means for temporarily securing the sterile drape on the housing may comprise an elastically deformable, surrounding seal, which produces a force on the sterile drape in a direction perpendicular to the surface of the housing during the positioning of the adapter. The method further comprises positioning the sterile drape adjacent the housing of the X-ray diagnosis system, and puncturing the sterile drape with the puncturing means of the adapter. The method further comprises securing the sterilizable localizing unit to the housing with the positioning means of the adapter, whereby the sterile drape is temporarily secured with the seal.

BRIEF DESCRIPTION OF THE DRAWINGS

The following drawings and the associated descriptions are provided to illustrate embodiments of the present disclosure and do not limit the scope of the claims.

DETAILED DESCRIPTION OF PREFERRED EMBODIMENTS

Figure 1:
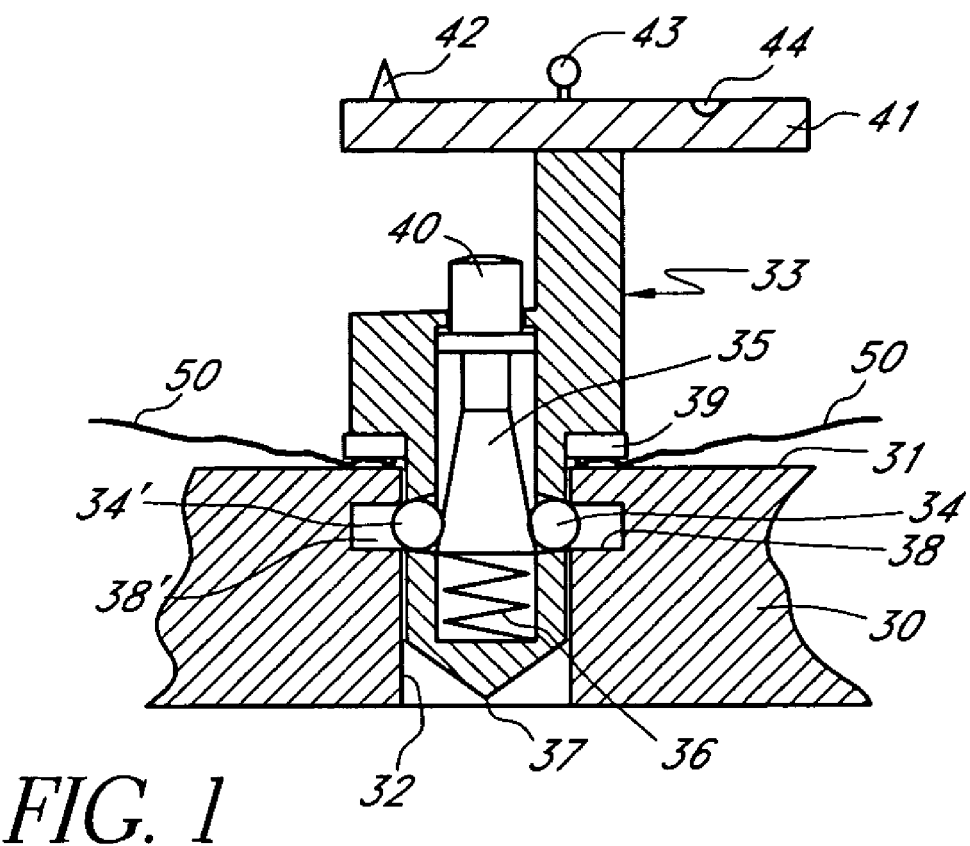
FIG. 1 is a partial sectional view schematically illustrating an embodiment of an X-ray diagnostic system and an embodiment of a localizing unit having an adapter for a sterile drape.

FIG. 1 is a partial sectional view schematically illustrating an embodiment of an X-ray diagnostic system and an embodiment of an adapter 33 for a sterile drape. The adapter 33 comprises a holding plate 41, which is attached to an upper side of the adapter 33. The holding plate 41 includes marks 42, 43, 44. The marks 42, 43, and 44 may have different shapes and/or configurations. The marks 42-44 can be detected by position detection systems of different types. The marks 42-44 may be positioned and/or oriented in a predetermined arrangement relative to the coordinate system of the adapter 33. The adapter 33 has a lower portion that can be received by a borehole 32 in a housing of the diagnostic system. The lower portion of the adapter 33 comprises a tip 37 that can be used to puncture a sterile drape 50.

Figure 2:
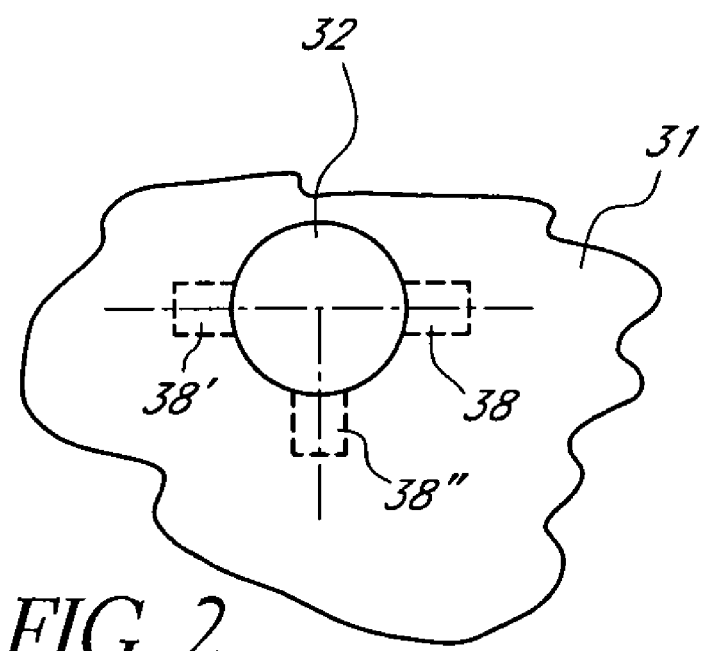
FIG. 2 is a partial top view schematically illustrating the system shown in FIG. 1.

In the embodiment shown in FIGS. 1 and 2, the housing 30 of the X-ray diagnostic system includes openings 38, 38', and 38" that align with corresponding conical openings formed in the adapter 33. When the lower portion of the adapter 33 is received in the borehole 32, a spring 36 and a cone 35 cause substantially spherical ball bearings 34, 34', and 34" to be pressed radially outward relative to the axis of the cone 35. The ball bearings 34, 34', and 34" are urged into engagement with the openings 38, 38', and 38", respectively, which locks the adapter 33 into place relative to the housing 30. The adapter 33 is configured to be removable from the housing 30. In the illustrated embodiment, the cone 35 is connected to a depressible pushbutton 40. When the pushbutton 40 is pressed in the direction of the tip 37, the spring 36 compresses, and the cone 35 moves toward the tip 37. Movement of the cone 35 provides a radial clearance for the spheres 34, 34', 34", thereby unlocking the adapter 33 from the housing 30 and allowing the adapter 33 to be removed from the borehole 32. In some embodiments, the adapter 33 has an elastically compressible seal 39, which presses the sterile drape 50 against a surface 31 of the housing 30 (when the adapter 33 is inserted in the borehole 32). The seal 39 advantageously may prevent displacement of the sterile drape 50 relative to the housing 30.

Figure 3:
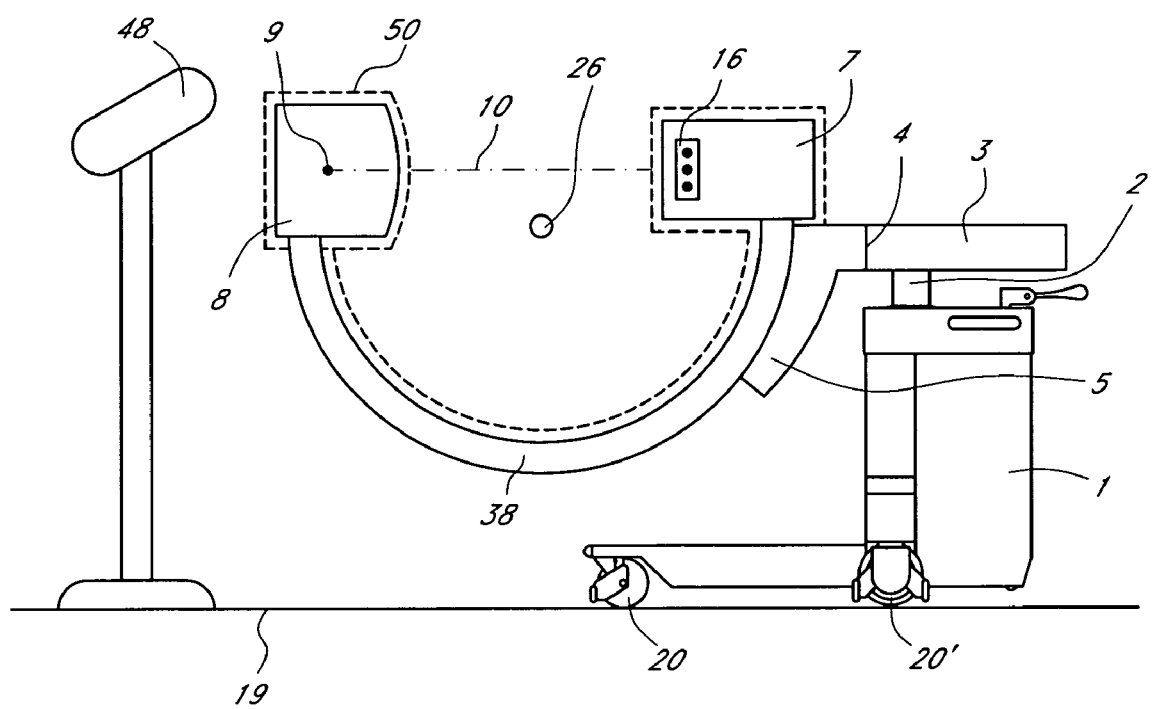
FIG. 3 schematically illustrates an embodiment of a surgical X-ray diagnostic system covered in part with a sterile drape.

FIG. 3 schematically illustrates an embodiment of a surgical X-ray diagnostic system covered in part with a sterile drape 50. In this embodiment, the X-ray diagnostic system comprises a C-arm 6 (with center 26) having opposing ends with an X-ray source 8 and an X-ray receiver 7. The X-ray source 8 emits X-rays from focus 9 along central ray 10 toward the X-ray receiver 7. The C-arm 6 is supported by a mount 5, which is configured to permit adjustment of the C-arm 6. The X-ray diagnostic system also comprises a cart 1 that moves on rollers 20, 20' along the floor 19. The mount 5 is attached to the cart 1 with a pivot 4 on the horizontal guide 3, which is coupled to the cart 1 by vertical column 2.

As shown in FIG. 3, the X-ray source 8, the C-arm 6, and the X-ray receiver 7 are covered (at least in part) with a sterile drape 50. A multipiece sterile drape 50 is preferred. The X-ray receiver 7 may include a mark configuration 16, whose position can be detected with a position detection system 18.

Figure 4A:
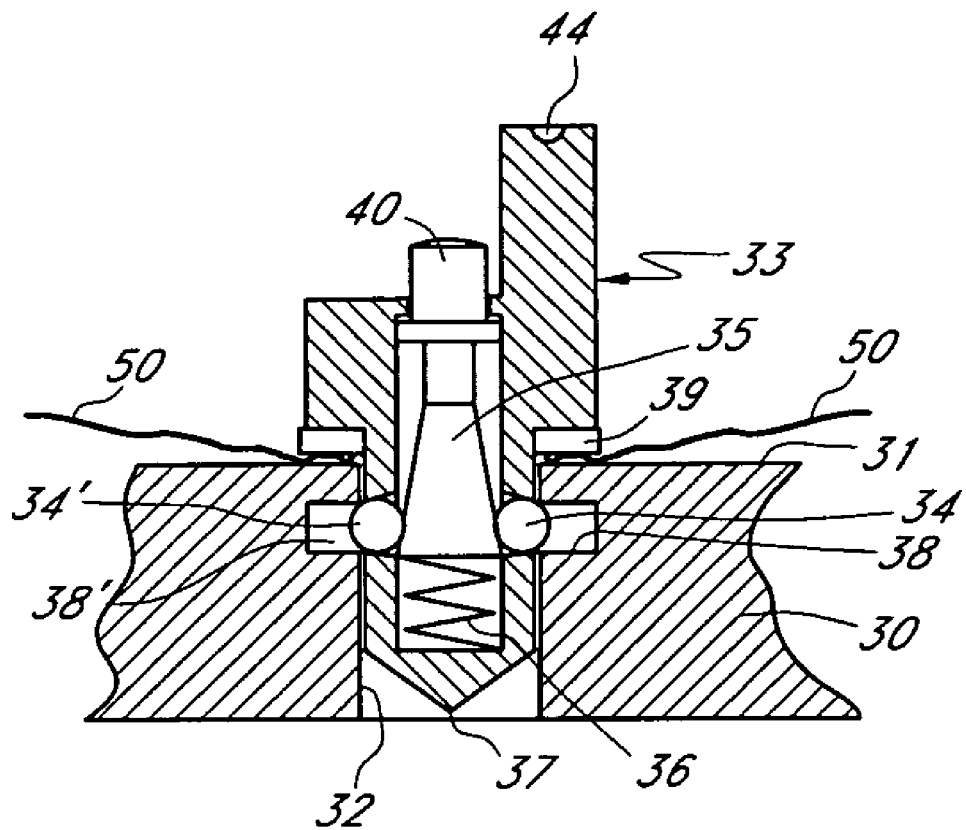
FIGS. 4a and 4b schematically illustrate alternative embodiments of an adapter for use with a sterile drape.
Figure 4B:
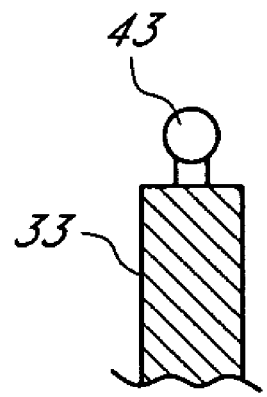

FIGS. 4a and 4b schematically illustrate alternative embodiments of an adapter 33 for use with a sterile drape 50. In the embodiment of the adapter 33 shown in FIG. 4a, a mark 44 of the third type shown in FIG. 1 is provided on the upper end of the adapter 33. The mark 44 can be scanned with a pointer of a position detection system 18. In the embodiment of the adapter 33 shown in FIG. 4b, a mark 43 of the second type shown in FIG. 1 is provided on the upper end of the adapter 33. In some embodiments, the mark 43 comprises an auto-reflection target (e.g., an auto-reflection sphere) or a light source (e.g., an LED light source) that can be used with an optical position detection system 18. In various embodiments, the marks 42, 43, 44 may be detachably held on the adapter 33 (and/or on the holding plate 41 shown in FIG. 1)

Embodiments of the adapter 33 may provide various features and advantages. For example, embodiments of the adapter 33 may be positioned on the housing 30 in a reproducible manner because the lower portion of the adapter 33 engages the openings 38, 38', and 38" in the housing 30 (see, e.g., FIGS. 1 and 4a). The adapter 33 may include a locking mechanism, which permits the adapter 33 to be temporarily secured to the housing 30. In some embodiments, the adapter 33 can be detached from the housing 30 by actuating a pushbutton 40 (see, e.g., FIGS. 1 and 4a). Embodiments of the adapter 33 may include some or all of the marks 42, 43, and 44 (see, e.g., FIGS. 1, 4a, and 4b).

Embodiments of the adapter 33 may comprise means for puncturing and for temporarily securing the sterile drape 50 on the housing 30 of the X-ray diagnostic device. For example, the means for puncturing may comprise a pointed tip 32, and the means for temporarily securing may comprise the compressible seal 39. In some implementations, embodiments of the adapter 33 may be used as follows. The sterile drape 50 is placed over the housing 30. The adapter 33 is then positioned with the seal 39 over the borehole 32. The tip 37 is pressed against the drape 50 causing the drape 50 to puncture. The adapter 33 is locked into position in the borehole 32, and the sterile drape is secured on the housing 30 by the compressed seal 39.

In certain embodiments, the borehole 32 in the housing 30 is threaded, and the lower portion of the adapter 33 comprises corresponding threads adapted to engage the borehole threads. The adapter 33 may be detachably positioned on the housing 30 by screwing the lower portion into the borehole 32. The adapter 33 may comprise a stop shoulder to limit how far the adapter 33 can be screwed into the borehole 32. In order to reduce twisting of the seal 39 during insertion of the adapter 33 into the threaded borehole 32, in some embodiments a washer is provided between the seal 39 and the adapter 33. In certain embodiments, the washer is integrated with the seal 39.

Although described herein in the context of an X-ray diagnostic system, a person of ordinary skill will recognize that embodiments of the disclosed adapter 33 may be used to secure sterile drapes to other medical devices. In any method or process disclosed herein, the acts or operations of the method or process may be performed in any suitable sequence and are not necessarily limited to any particular disclosed sequence. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner in one or more embodiments, as would be apparent to one of ordinary skill in the art from this disclosure. Additionally, although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above.

What is claimed is:

1. A sterilizable localizing unit adapted for detachable and reproducible positioning on a housing of a nonsterile surgical X-ray diagnosis system, which is covered at least in part with a sterile drape, the localizing unit comprising an adapter having at least one mark that can be detected by a position detection system, characterized in that the adapter comprises means for puncturing the sterile drape, means for the detachable and reproducible positioning of the adapter on the housing, and means for temporarily securing the sterile drape on the housing while the adapter is positioned on the housing, wherein the means for temporarily securing the sterile drape on the housing comprises an elastically deformable, surrounding seal, which produces a force on the sterile drape in a direction perpendicular to the surface of the housing during the positioning of the adapter, further characterized in that the means for the detachable and reproducible positioning of the adapter comprises a pushbutton with which the adapter can be locked or unlocked with respect to the housing, the pushbutton comprising a spring, a cone, and one or more ball bearings, the spring providing a resistance force against the pushbutton.

2. The sterilizable localizing unit according to claim 1, characterized in that the adapter comprises a holding plate comprising one or more marks that are arranged in predetermined positions relative to a coordinate system of the adapter.

3. The sterilizable localizing unit according to claim 1, characterized in that the adapter comprises at least one mark capable of being scanned by a pointer of the position detection system.

4. The sterilizable localizing unit according to claim 1, characterized in that the adapter has at least one mark that comprises an auto-reflection target capable of being detected by the position detection system.

5. An adapter for removably attaching a sterile drape to a medical diagnostic system, the adapter comprising:
- a lower portion configured for removable attachment to a borehole in a housing of the medical diagnostic system, the lower portion comprising a tip configured to puncture the sterile drape, the lower portion comprising a locking mechanism configured to releasably lock the adapter into a predetermined position on the medical diagnostic system;
- an upper portion having one or more markers ca able of being detected by a position detection system; and a seal configured to secure a portion of the sterile drape between a portion of the adapter and the housing of the medical diagnostic system, wherein the locking mechanism comprises a pushbutton actuatable between a locked position and an unlocked position, the pushbutton comprising a user-actuatable button, a conical member capable of moving along a longitudinal axis, a spring configured to provide a spring force along the longitudinal axis, and one or more ball bearings capable of moving radially toward and away from the longitudinal axis in response to movement of the conical member.

6. The adapter of claim 5, wherein when the pushbutton is in the locked position, an outer surface of the conical member provides a radial-directed force on the one or more ball bearings.

7. The adapter of claim 6, wherein when the pushbutton is in the unlocked position, the button is depressed thereby moving the conical member in the longitudinal direction and thereby reducing the radial-directed force on the one or more ball bearings.

8. The adapter of claim 5, wherein the seal comprises an elastically deformable material.

* * * * *